United States Patent
Fogarty et al.

(10) Patent No.: US 6,558,408 B1
(45) Date of Patent: May 6, 2003

(54) SURGICAL CLAMP HAVING REPLACEABLE PAD

(75) Inventors: Thomas J. Fogarty, Portola Valley, CA (US); Thomas A. Howell, Palo Alto, CA (US); David Willis, Palo Alto, CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 31 days.

(21) Appl. No.: 09/675,722

(22) Filed: Sep. 29, 2000

Related U.S. Application Data (62) Division of application No. 09/336,131, filed on Jun. 18, 1999, now Pat. No. 6,228,104.

(51) Int. Cl.[7] .............................................. A61B 17/28
(52) U.S. Cl. ...................................... 606/207; 606/151
(58) Field of Search ................................. 606/205–210, 606/147, 151, 158, 148, 157, 139

(56) References Cited

U.S. PATENT DOCUMENTS

| | | | |
|---|---|---|---|
| 1,048,937 A | 12/1912 | Brightwell | |
| 2,743,726 A | 5/1956 | Grieshaber | 128/321 |
| 3,446,211 A | 5/1969 | Markham | 128/322 |
| 3,503,396 A | 3/1970 | Pierie et al. | 128/322 |
| 3,503,397 A | 3/1970 | Fogarty et al. | 128/322 |
| 3,503,398 A | 3/1970 | Fogarty et al. | 128/322 |
| 3,746,002 A | 7/1973 | Haller | 128/322 |
| 3,880,166 A | 4/1975 | Fogarty | 128/325 |
| 3,993,076 A | 11/1976 | Fogarty | 128/325 |
| 4,120,302 A | 10/1978 | Ziegler | 128/322 |
| 4,548,202 A | 10/1985 | Duncan | 128/334 |
| 4,611,593 A | 9/1986 | Fogarty et al. | 128/325 |
| 4,768,687 A | 9/1988 | Ault | 223/116 |
| 4,821,719 A | 4/1989 | Fogarty | 128/325 |
| 4,955,897 A | 9/1990 | Ship | 606/210 |
| 5,171,253 A | 12/1992 | Klieman | 606/158 |
| 5,217,460 A | 6/1993 | Knoepfler | 606/52 |
| 5,279,416 A | 1/1994 | Malec et al. | 206/339 |
| 5,308,358 A | 5/1994 | Bond et al. | 606/205 |
| 5,397,324 A | 3/1995 | Carroll et al. | |
| 5,535,756 A | 7/1996 | Parasher | 128/756 |
| 5,569,274 A | 10/1996 | Rapacki et al. | 606/158 |
| 5,582,615 A | 12/1996 | Foshee et al. | 606/139 |
| 5,591,182 A | 1/1997 | Johnson | 606/151 |
| 5,624,454 A | 4/1997 | Palti et al. | 606/151 |
| 5,728,121 A | 3/1998 | Bimbo et al. | |
| 5,772,670 A | 6/1998 | Brosa | 606/108 |
| 5,843,101 A | * 12/1998 | Fry | 606/157 |
| 5,855,590 A | 1/1999 | Malecki et al. | |
| 6,099,539 A | * 8/2000 | Howell et al. | 606/207 |

FOREIGN PATENT DOCUMENTS

| | | | |
|---|---|---|---|
| CH | 65626 | 8/1913 | |
| DE | 29921622 U1 | 3/2000 | |
| EP | 0 490 301 A1 | 6/1992 | A61B/17/28 |
| WO | WO 98/33437 | 8/1998 | A61B/17/00 |

OTHER PUBLICATIONS

Aesculap catalog (1997), selected excerpts.

Baxter model DSAFEE33,, Double Safe Jaw brand insert set.

* cited by examiner

*Primary Examiner*—Kevin T. Truong
(74) *Attorney, Agent, or Firm*—Morrison & Foerster LLP (57) ABSTRACT

A surgical clamp having an elongate cavity to receive a replaceable pad. The pad includes a draw cord to draw the pad into place on the jaw. The pad is formed with an attachment member engagable in the elongate cavity of the jaw. The draw cord is preferably an extension of the attachment member.

9 Claims, 15 Drawing Sheets

SURGICAL CLAMP HAVING REPLACEABLE PAD

This is a divisional of application Ser. No. 09/336,131, filed Jun. 18, 1999 now U.S. Pat. No. 6,228,104.

BACKGROUND OF THE INVENTION

1. Field of the Invention

The present invention relates to surgical clamps. In particular, the invention relates to surgical clamps having replaceable pads.

2. Description of the Related Art

Surgical clamps exist in many sizes with many different types of clamp shapes (e.g., curved jaws, straight jaws, etc.). In addition, many different types of jaw surfaces exist, as adapted to the specific function performed by the clamp. When a different function is to be performed, either one must use a different clamp, or in some circumstances replaceable pads may be added to the jaws.

Many existing surgical clamps have jaws with hard clamping surfaces. Some replaceable pads for these clamps are designed to fit over the jaws to provide a softer clamping surface. However, these pads are often bulky, reducing the sleekness of the clamp and jaws. In addition, these pads are typically designed to fit over only straight jaws and are generally straight themselves, so there is a need for other shapes such as curved or S-shaped.

Other existing surgical clamps have curved, replaceable pads that are sleek, but these sleek pads are not soft and may be inappropriate for many applications.

Still other existing surgical clamps have soft pads but these pads are not replaceable. This makes the pads harder to clean. Autoclaving may cause soft or delicate pads to deteriorate or wear out more quickly; with the result that the pad surfaces may become less soft or less delicate. As an alternative, the pad surfaces may be constructed to as to be less soft or less delicate in order to have a longer lifetime.

Some surgical clamps (e.g., U.S. Pat. No. 3,503,398) have replaceable pads that are soft, but have other concerns. The pads are installed from the distal end, and may slip off from that direction. Decreasing the possibility of the pads slipping off may increase the effort necessary to install the pads. In addition, the portion of the pad that attaches to the clamp may not be flexible.

Finally, some existing surgical clamps have replaceable pads that are not tightly secured to the jaws. With such clamps, the pads may move laterally after the vessel or tissue has been clamped. This lateral movement makes for an insecure clamp subject to wobbling, that may shear the vessel or tear the tissue. So there is a need to tightly secure the pads to the jaws.

SUMMARY OF THE INVENTION

The present invention addresses these and other problems of existing devices by providing a surgical clamp having a jaw with an elongate cavity to receive a replaceable pad. The pad includes a draw cord to draw it into the cavity.

According to one embodiment, the surgical clamp of the present invention comprises a pair of elongate jaws connected together for movement toward each other, at least one of the jaws having an outer surface in opposition to the other jaw. An elongate cavity extends longitudinally within the jaw. The cavity is adapted for slidably receiving a clamp pad. An elongate channel opens through the outer surface and longitudinally connects the cavity to the outer surface. The channel is generally commensurate with the cavity longitudinally.

The invention is also directed to a method of making a replaceable pad, the method comprising the steps of providing a flexible elongate attachment member, and forming a pad around the attachment member.

The invention also provides a method of installing a replaceable pad in the jaw of a surgical clamp, the method comprising the steps of providing a pad having a flexible elongate attachment member, and a draw cord extending generally longitudinally from the pad, and providing a surgical clamp having at least one elongate jaw with an outer clamping surface. The jaw has an elongate cavity extending longitudinally therein and a hole opening therefrom at one end of the cavity. The cavity is configured to slidably receive the attachment member. The method also includes the steps of inserting the draw cord into the cavity, directing the draw cord through the hole, and applying tension to the draw cord to draw the attachment member into the cavity and secure the pad in place on the clamping surface of the jaw.

According to one embodiment, the replaceable pad of the present invention comprises an elongate body configured to extend over an outer surface of a jaw of a surgical clamp, and a flexible elongate attachment member connected to the body and configured for slidable receipt within an elongate cavity extending longitudinally of the jaw.

A principal object of these embodiments of the invention is to provide a surgical clamp with replaceable pads that are easily installable without special tools.

Another object is to provide a draw cord on the pad to allow a pulling force for easier installation.

Yet another object is to provide a surgical clamp with replaceable pads that resist lateral movement between the clamp and the pads.

Still another object is to provide a surgical clamp with replaceable pads that are sleek and compact.

A further object is to provide a surgical clamp with replaceable pads that are flexible such that one pad configuration may be used on a wide variety of jaw shapes.

These and other objects will become apparent when viewed in light of the following detailed description and accompanying drawings which set forth illustrative embodiments in which the principles of the invention are utilized.

DETAILED DESCRIPTION OF THE PREFERRED EMBODIMENTS

Figure 1:
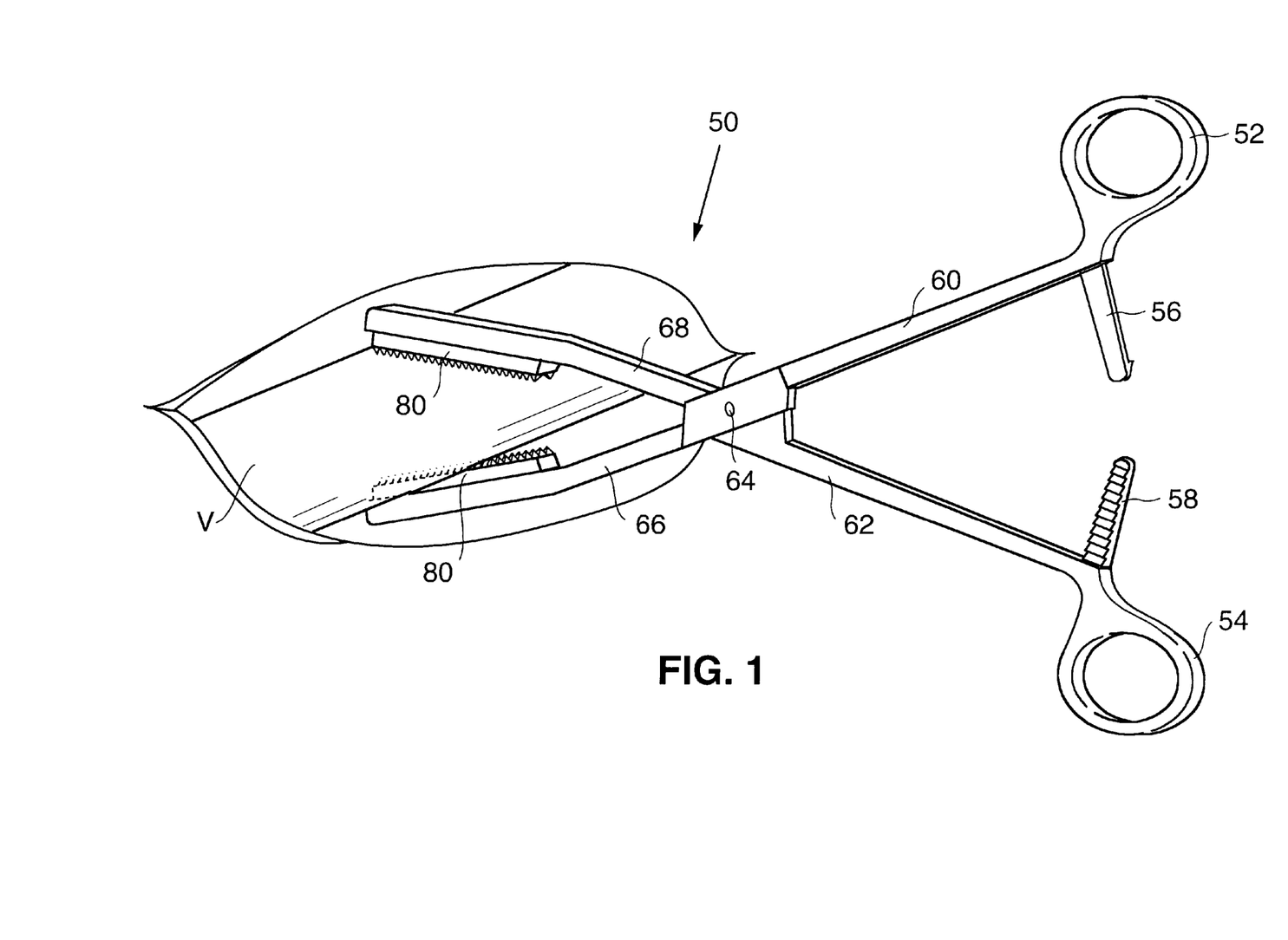
FIG. 1 is a perspective view of a surgical clamp constructed according to a first embodiment of the present invention.

FIG. 1 shows an exemplary surgical clamp 50 according to one embodiment of the present invention. The clamp 50 is shown in the process of clamping a vessel V. It may also be used to clamp organs or other bodily tissue.

The clamp 50 includes finger and thumb rings 52 and 54 for operating the clamp. A pawl 56 and ratchet teeth 58 lock the clamp 50 when it is applied to vessel V. Handles 60 and 62 are pivotally connected by pin 64. Jaws 66 and 68 apply the clamping force to vessel V, as cushioned by pads 80.

Figure 2:
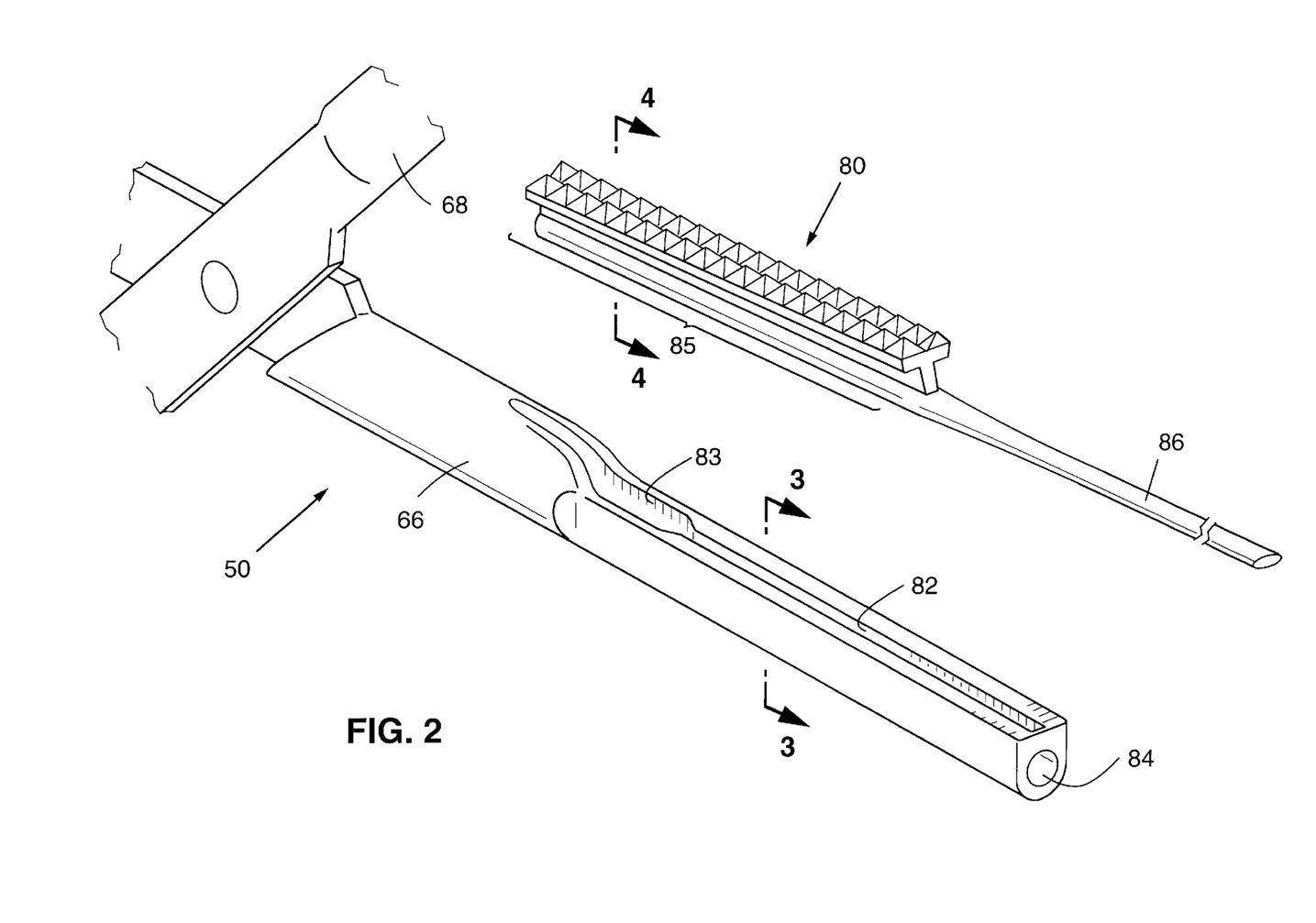
FIG. 2 is an exploded perspective view of a jaw of the surgical clamp of FIG. 1, with parts thereof broken away, showing a detached pad for the clamp.

FIG. 2 shows an enlarged view of the jaw 66 and the pad 80 in a detached condition. A channel 82 extends longitudinally along the jaw 66. The channel 82 forms a groove communicating with a generally cylindrical cavity 90 within the jaw 66 coextensive with the groove. One end of the channel 82 forms an enlarged mouth 83 opening into the cavity 90. The end of the cavity 90 opposite the mouth 83 is formed with a hole 84. A draw cord 86 for the pad 80 passes through the hole 84 when the pad 80 is attached to the jaw 66, as more fully described with reference to FIGS. 5–9 and the accompanying text. An attachment member 85 is coextensive with the pad 80 and is preferably a portion of the draw cord 86. The draw cord 86 may also be referred to as a filament.

Figure 3:
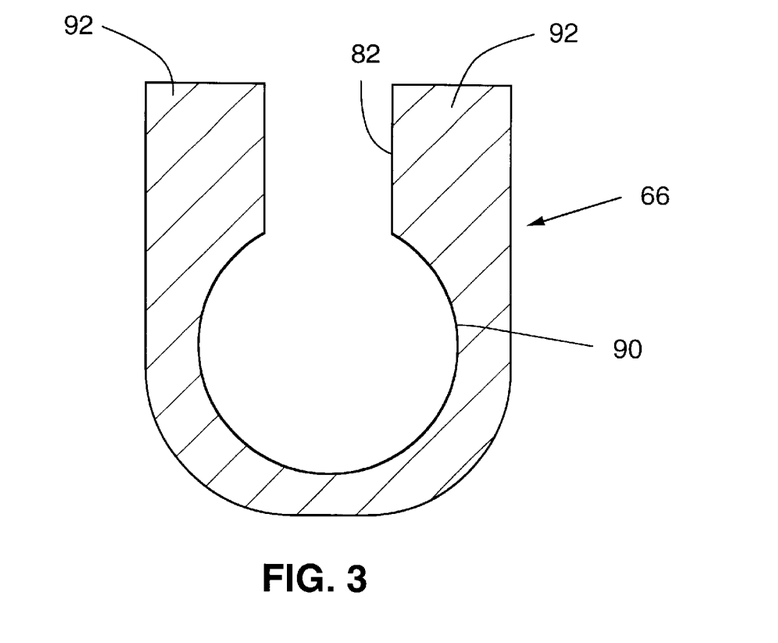
FIG. 3 is a cross-sectional view taken on the plane designated by line 3—3 of FIG. 2.

FIG. 3 is a cross-section of the jaw 66 taken on line 3—3 of FIG. 2. The jaw 66 has a generally U-shaped lower surface for smoothness. The cavity 90 extends longitudinally within the jaw 66. The channel 82 connects the cavity 90 to outer surfaces 92 of the jaw 66. The outer surfaces 92 are generally flat to facilitate installation of the pad 80, and may be angled. The angling helps keep the pad 80 from moving laterally with respect to the jaw 66. The cavity 90 has a larger cross-sectional width than the channel 82, to secure the pad 80 within the cavity 90.

Figure 4:
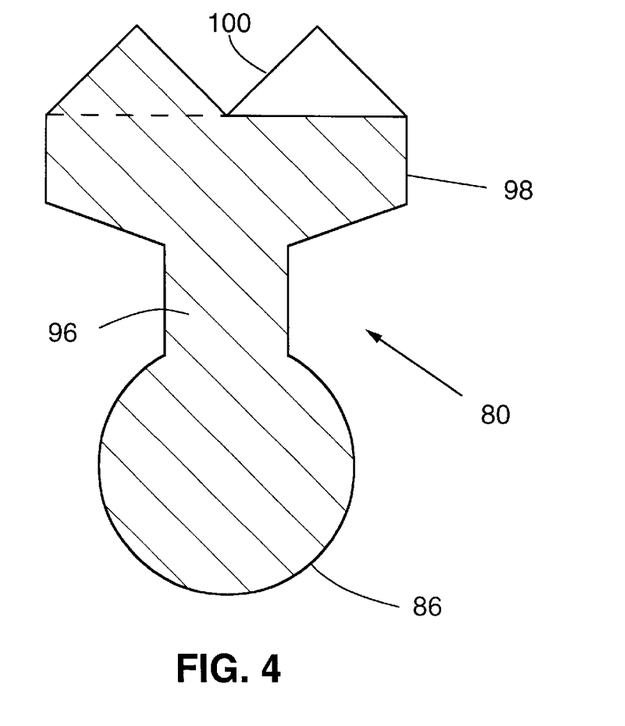
FIG. 4 is a cross-sectional view taken on the plane designated by line 4—4 of FIG. 2.

FIG. 4 is a cross-section of the pad 80 taken on line 4—4 of FIG. 2. A neck 96 connects the draw cord 86 to a pad body 98. The pad body 98 fits against the outer surfaces 92 (see FIG. 3) when the pad 80 is attached to the jaw 66. The draw cord 86 fits within the cavity 90 (see FIG. 3) when the pad 80 is attached to the jaw 66. The neck 96 may be slightly shorter than the channel 82 (see FIG. 3) so that when the pad 80 is attached to the jaw 66, the pad body 98 is pulled tightly against the outer surfaces 92, to inhibit lateral movement therebetween. Alternatively, the neck 96 may fist snugly within the channel 82 to inhibit lateral movement between the pad body 98 and the outer surfaces 92. Reducing lateral movement between the pad 80 and the jaw 66 is important to minimize wobbling of the pad relative to the jaw and reduce possible trauma resulting from application of the clamp 50 to bodily tissues, organs or vessels.

The neck 96 is preferably made of a thermoplastic elastomer, as further detailed below. The geometry and materials in the neck 96 may be modified for adjusting the fit in the channel 82. For example, the neck 96 may be made from a relatively hard plastic or from a relatively soft plastic, or may be slightly wider than the channel 82.

The pad body 98 preferably has a clamping surface 100 as shown in FIG. 4 and as further detailed with reference to FIGS. 10–13 and the accompanying text. The particular structure is pyramidal, similar to that of Model DSAFE33 FOGARTY DOUBLE SAFEJAW insert set from Baxter Corp. However, pad body 98 may instead have a wide variety of other surfaces. For example, the surface may be hard, soft, smooth, bumpy, etc. as currently exist on other surgical clamps. The pad body 98 is preferably made of a thermoplastic elastomer, as further detailed below.

Pull string 86 may be a polyester monofilament with a diameter of 0.062 inches. Pull string 86 may also be nylon or polypropylene.

Figure 2A:
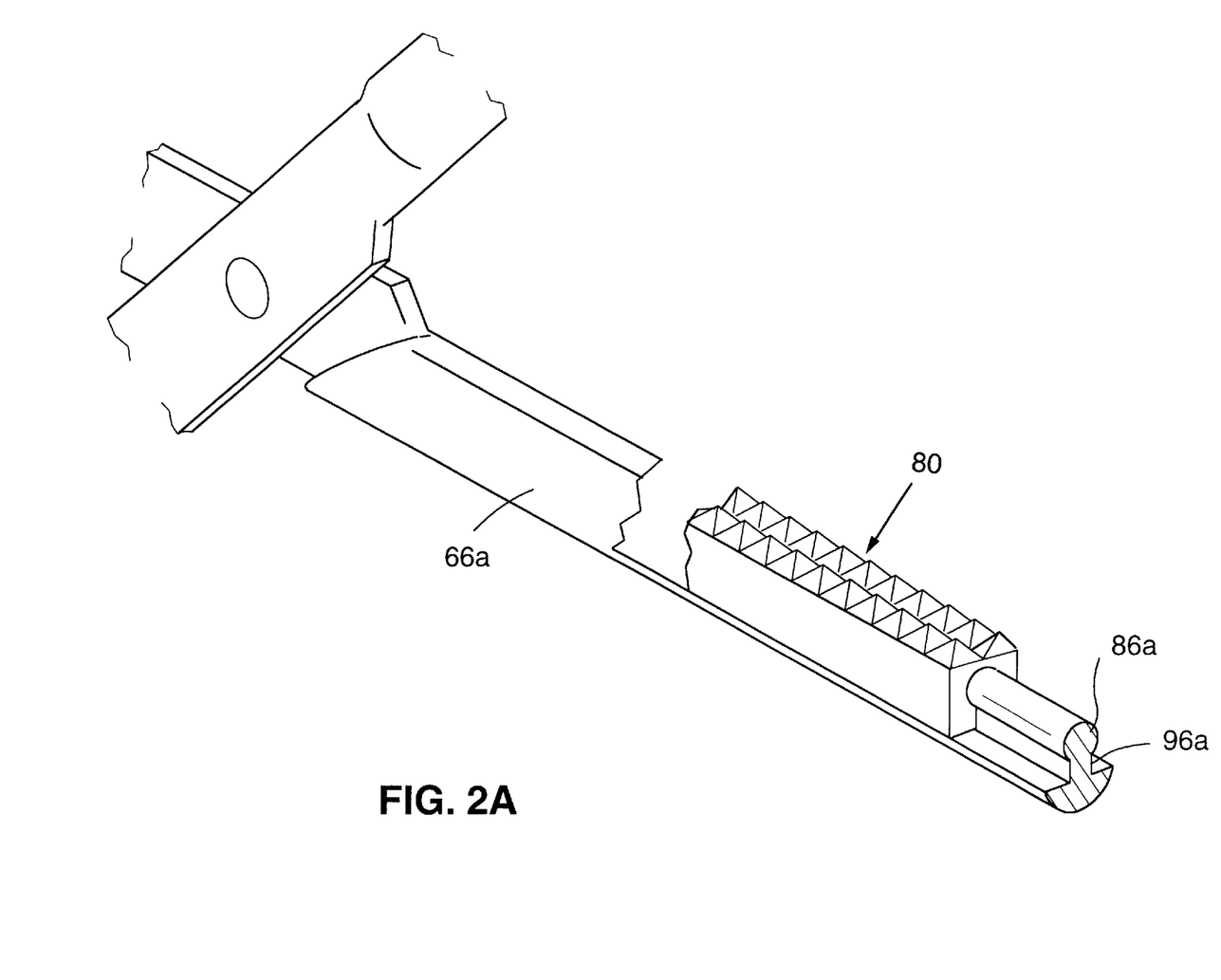
FIG. 2A is an exploded perspective view of a jaw according to a second embodiment of the present invention, with parts thereof broken away.

FIG. 2A shows a portion of a modified jaw 66a which may be referred to as a reverse or keyhole configuration. The jaw 66a includes a neck 96a and an attaching element 86a, with the attaching element wider than the neck. A pad 80 is adapted to attach to the neck 96a and the attaching element 86a, and is otherwise similar to pad 80. The pad 80a may be installed from the distal end or the proximal end of the jaw 66a.

Pad Attachment

Figure 5:
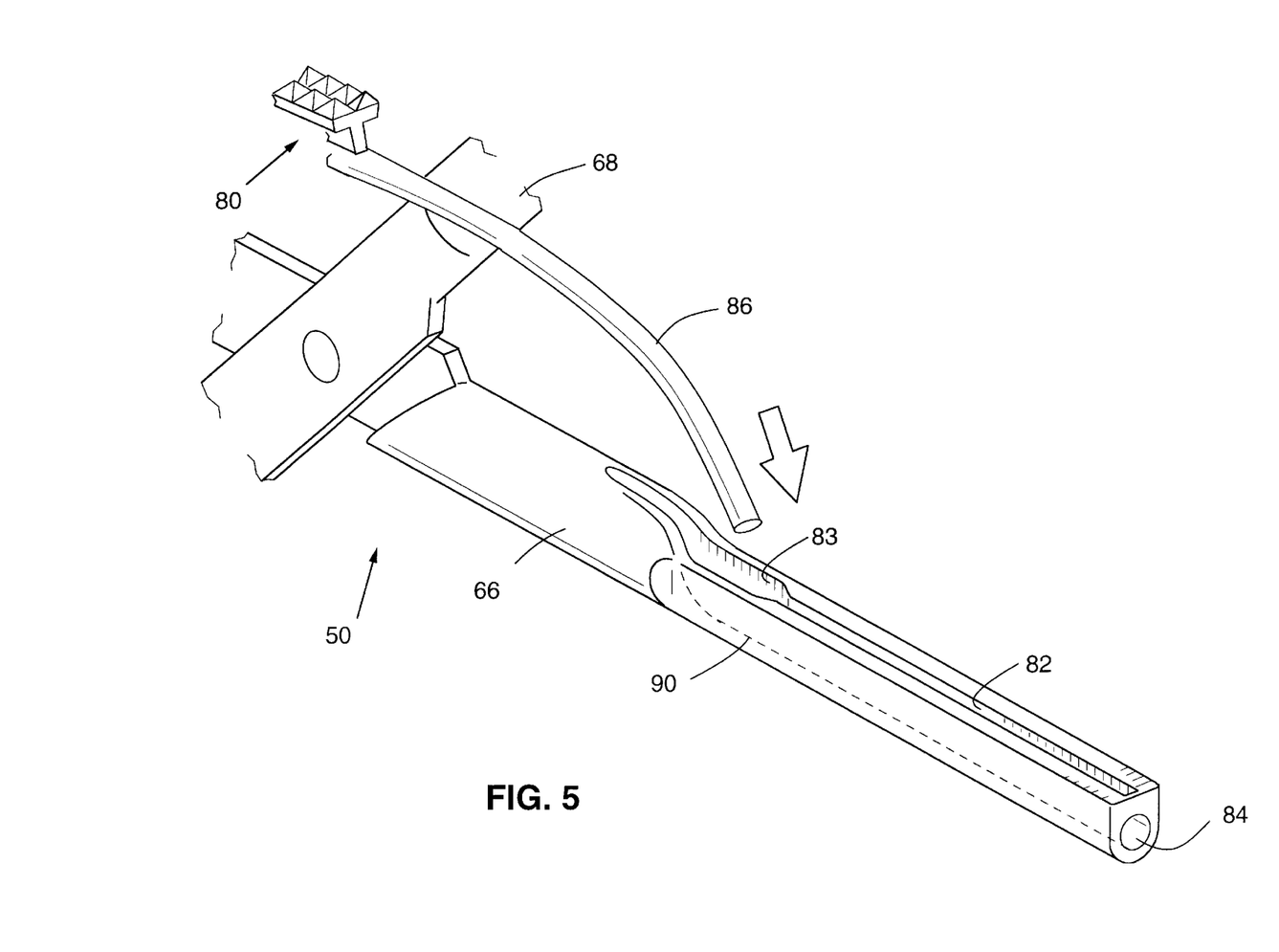
FIGS. 5–8 are enlarged perspective views of a jaw of the surgical clamp of FIG. 1, showing the steps of installing the pad in the jaw.
Figure 6:
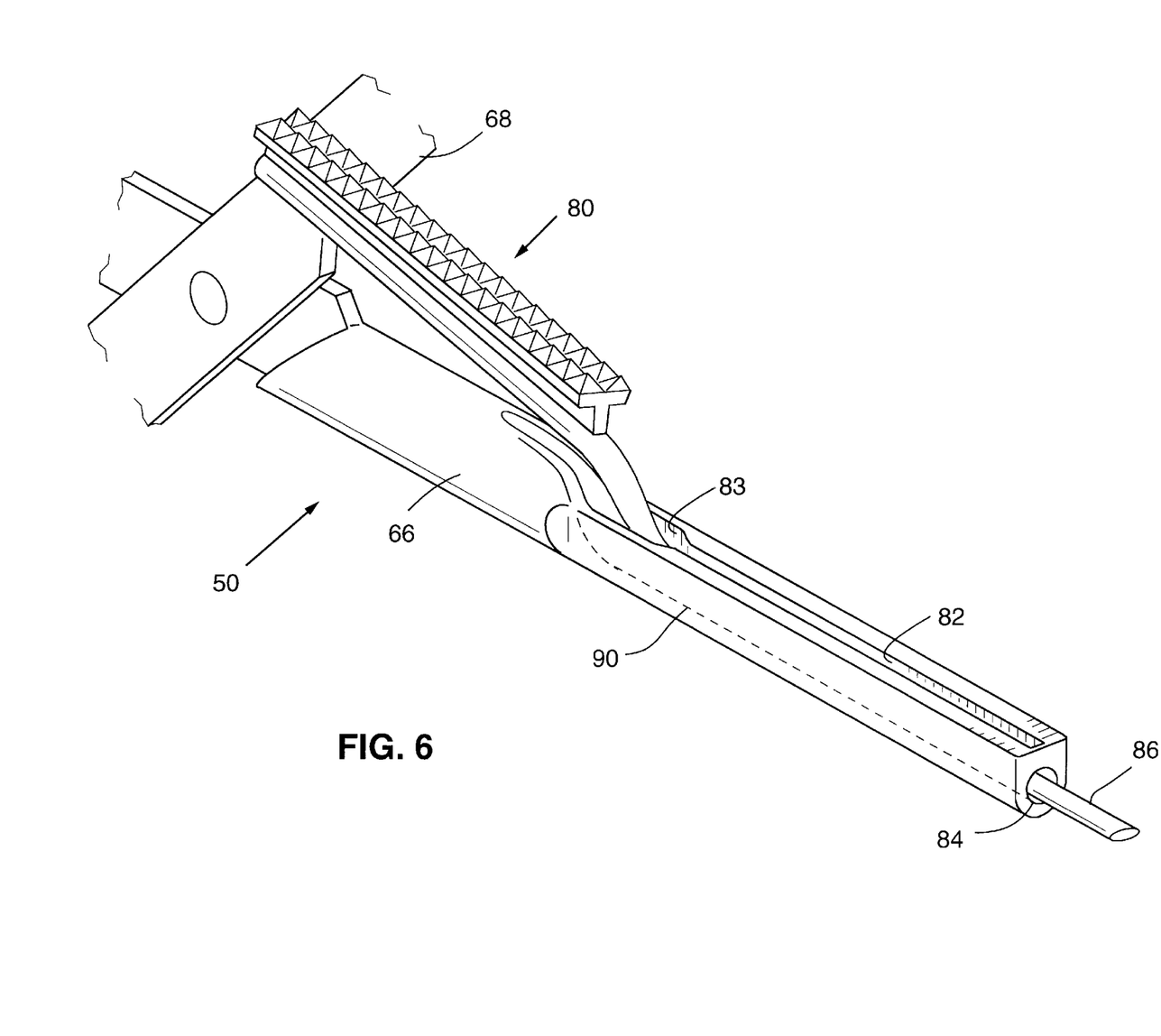

FIGS. 5–9 illustrate the steps for attaching the pad 80 to the jaw 66. FIG. 5 shows that a distal end of the draw cord 86 is inserted into the mouth 83 at the proximal end of the channel 82 and cavity 90. FIG. 6 shows that the draw cord 86 is fed through the cavity 90 until it emerges from the hole 84. At this point, the neck 96 is about to enter the channel 82.

Figure 7:
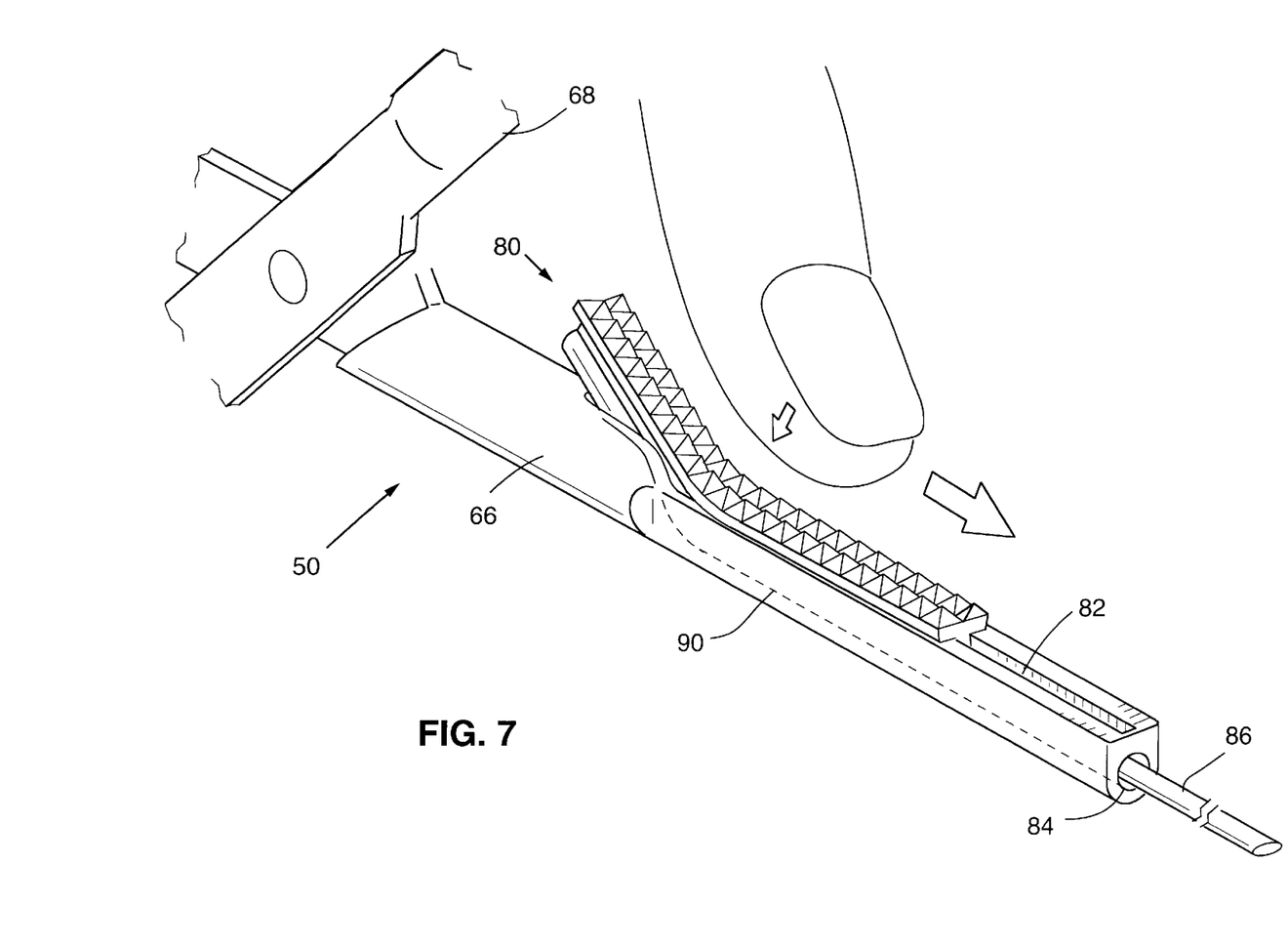

FIG. 7 shows the draw cord 86 being pulled to engage the pad 80 within the jaw 66, and shows the finger of a person installing the pad guiding the pad into the mouth 83. The draw cord 86 applies a generally uniform pulling force on the pad 80. This decreases the tendency for the pad 80 to expand at its distal end and bind against the inner surfaces of the cavity 90 and the channel 82, as would be likely from insertion with only a pushing force. Pad 80 may also be pushed by the finger during the engagement process. Such a combination of pushing and pulling allows the pad 80 to move through the inner surfaces of the jaw 66 better than pulling alone.

Note that the attachment member 85 flexes as it enters the mouth 83. This flexibility allows the attachment member 85 to be inserted into a cavity without requiring the cavity to be uniformly straight.

Figure 8:
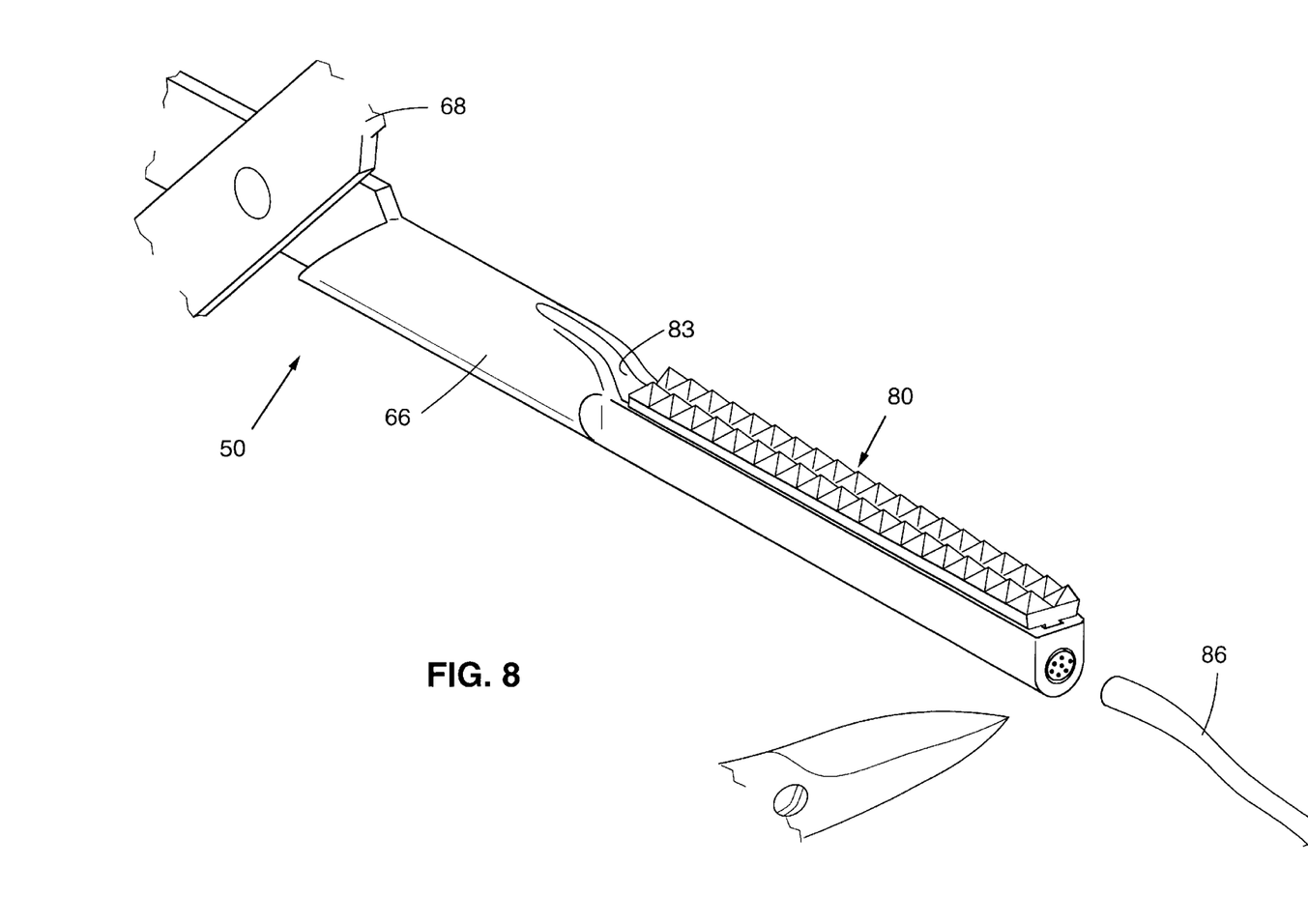
Figure 9:
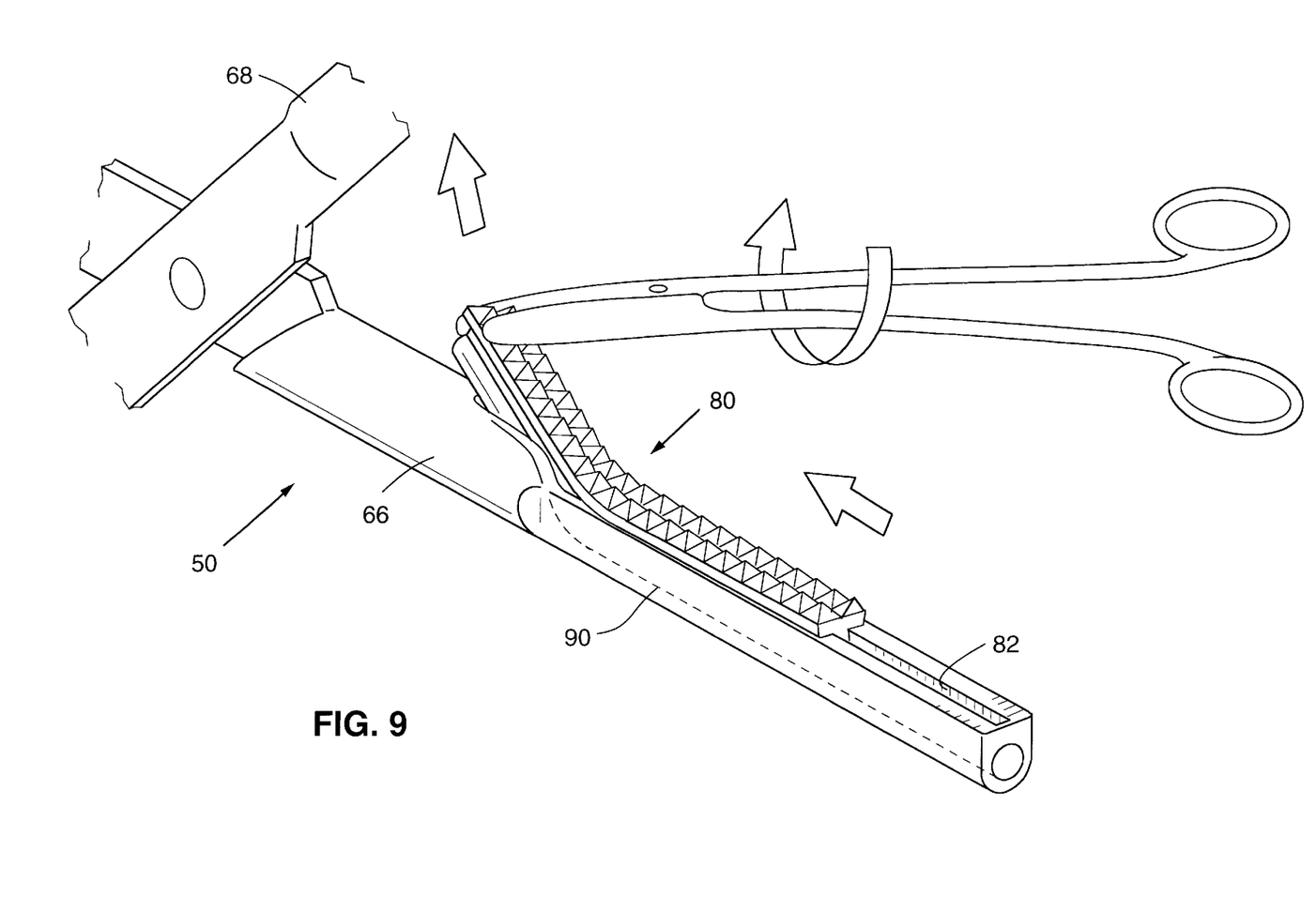
FIG. 9 is an enlarged perspective view of a jaw of the clamp of FIG. 1 showing the pad being removed from the jaw.

FIG. 8 shows the pad 80 fully engaged with the jaw 66 and the draw cord 86 being cut, as it is no longer needed. FIG. 9 shows that the pad 80 may be removed by grasping it at its proximal end with a grasping tool and applying a backward and upward force to draw the pad out of the mouth 83.

Besides the advantage of a generally uniform pulling force described above, the draw cord 86 has a number of other advantages. By fitting within the cavity 90, the draw cord 86 functions to attach the pad 80 to the jaw 66, so that a single structure (the draw cord 86) may perform both attaching and installation functions. The draw cord 86 enables attachment of the pad 80 to the jaw 66 without the need for special tools during installation.

Figure 15:
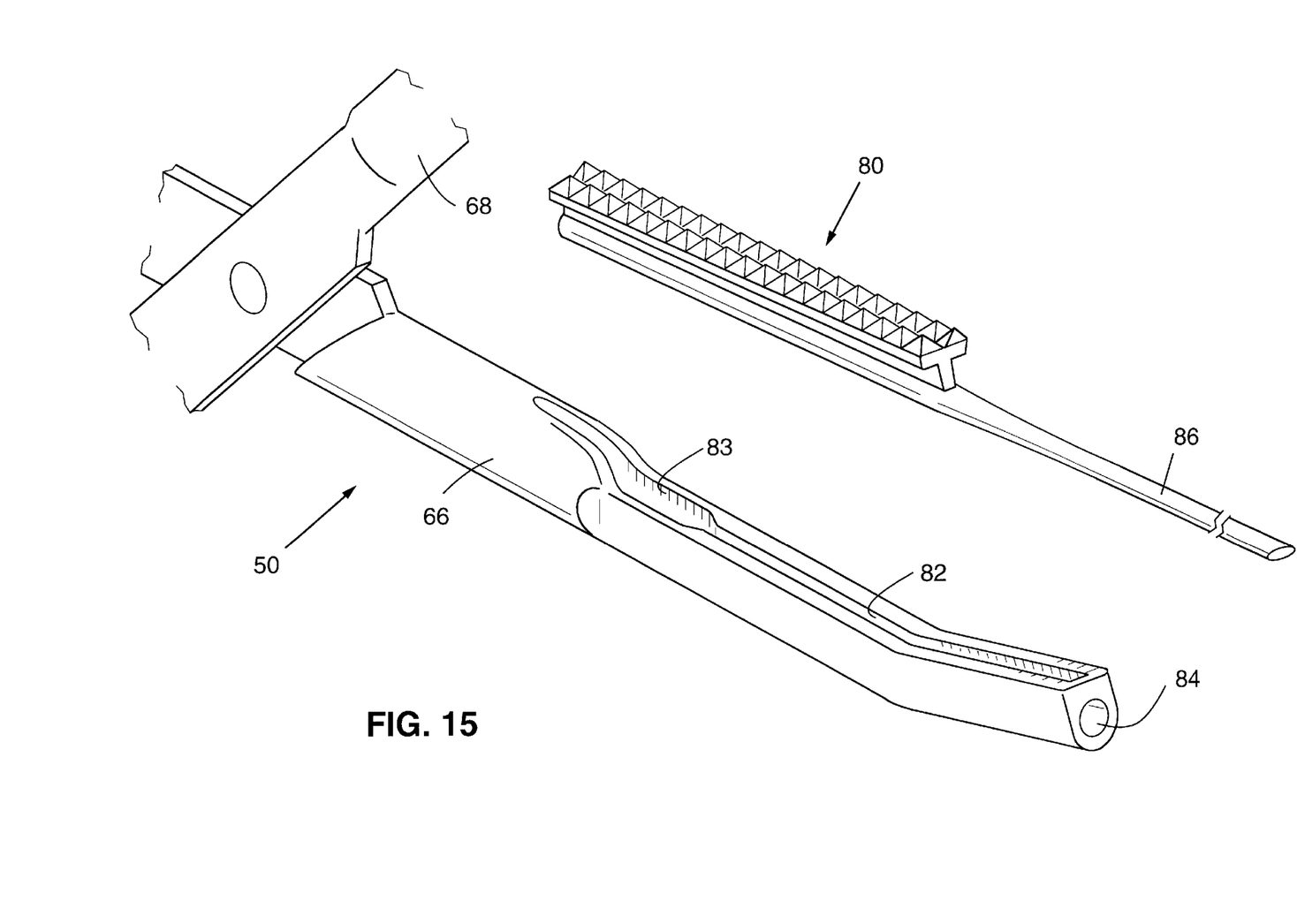
FIG. 15 is an exploded perspective view of a jaw of a surgical clamp according to a second embodiment of the present invention, with parts thereof broken away, showing a clamp with a curved jaw.

The provision of removable pads has a number of advantages over clamps without removable pads. Clamps with removable pads are easier to clean. The pads may be removed and the clamp autoclaved, then new pads installed. (Autoclaving may degrade or otherwise wear out soft or otherwise non-metallic parts of the clamp, so many clamps omit pads. Similarly, soft or otherwise fragile pads may wear out, so these may be easily replaced.) The pads may have different surfaces, so when a different surface is desired the appropriate pad may be easily installed. In addition, the pad 80 may be flexible for installation in curved or S-shaped jaws, as shown in FIG. 15. In such a case the same pad configuration may be used for a number of clamp shapes (straight, curved, S-shaped, etc.).

Pad Construction

Figure 10:
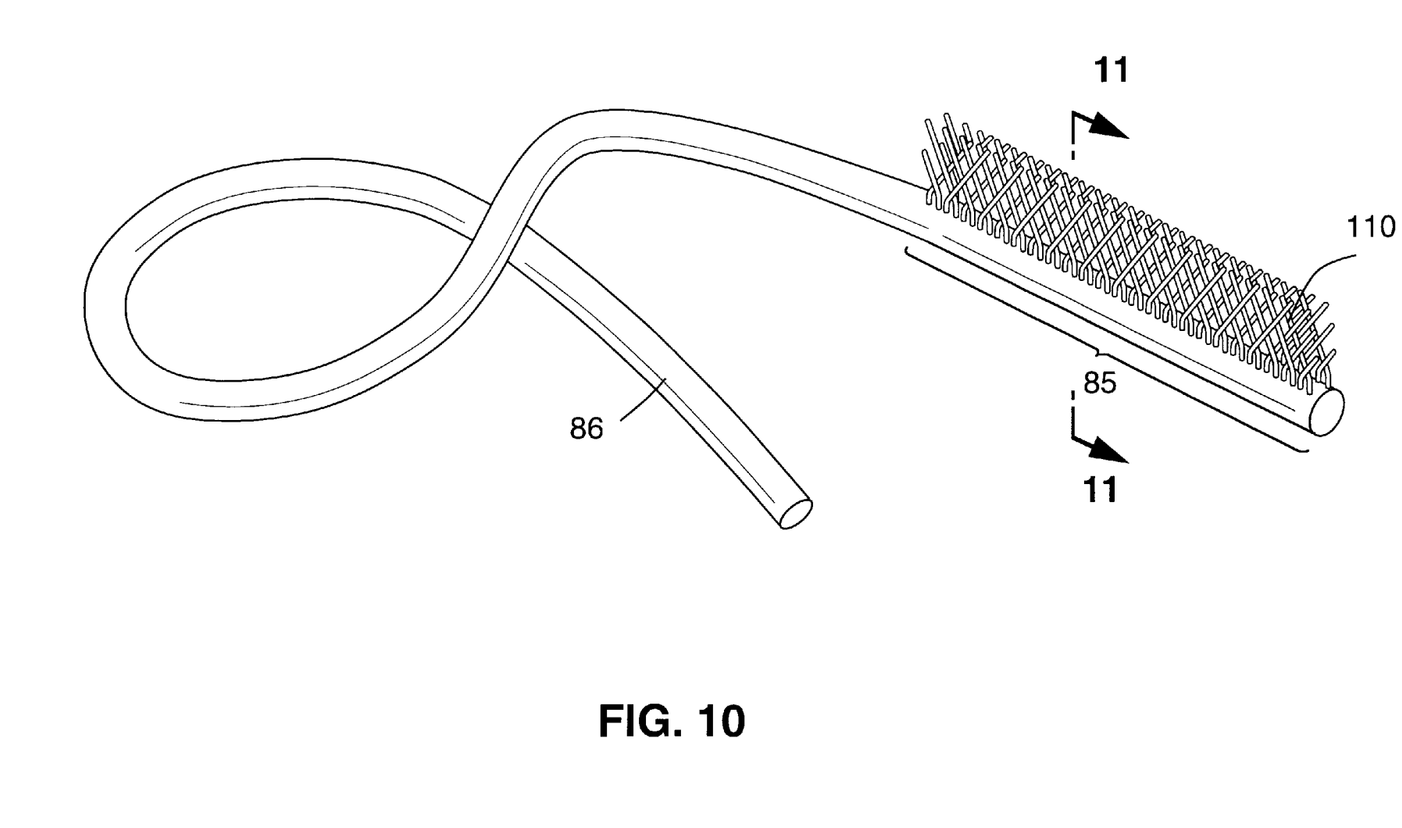
FIG. 10 is a perspective view of a draw cord with mesh for a first embodiment of the pad of the present invention.

FIGS. 10–13 illustrate various stages in the manufacture of the pad 80. FIG. 10 shows that the draw cord 86 may have a length of approximately 6–8 inches for all lengths of pads. The actual pad portion, as represented by a mesh 110, may have a length appropriate to the jaws to which the pad is to be installed. For example, the pad 80 may have a length from approximately 25 to 86 millimeters.

The mesh 110 may be a plain weave fabric (e.g., a filter cloth) and preferably has 46 threads per inch, with a range from approximately 20 to 100 threads per inch. A preferred material is nylon mesh from Sefar of Depew, N.Y. [Please verify the company name and location.] The mesh 110 is preferably cut on a bias of 45 degrees so that the threads extend at an angle from the direction of cutting.

In a preferred method of manufacture of the pad 80, the mesh 110 is folded in half longitudinally and placed in a longitudinal first mold, forming a V-shape. Then, nylon or polypropylene is injection molded in the fold to form the draw cord 86. The injection molding process also attaches the draw cord 86 to the threads of the mesh 110.

Figure 14:
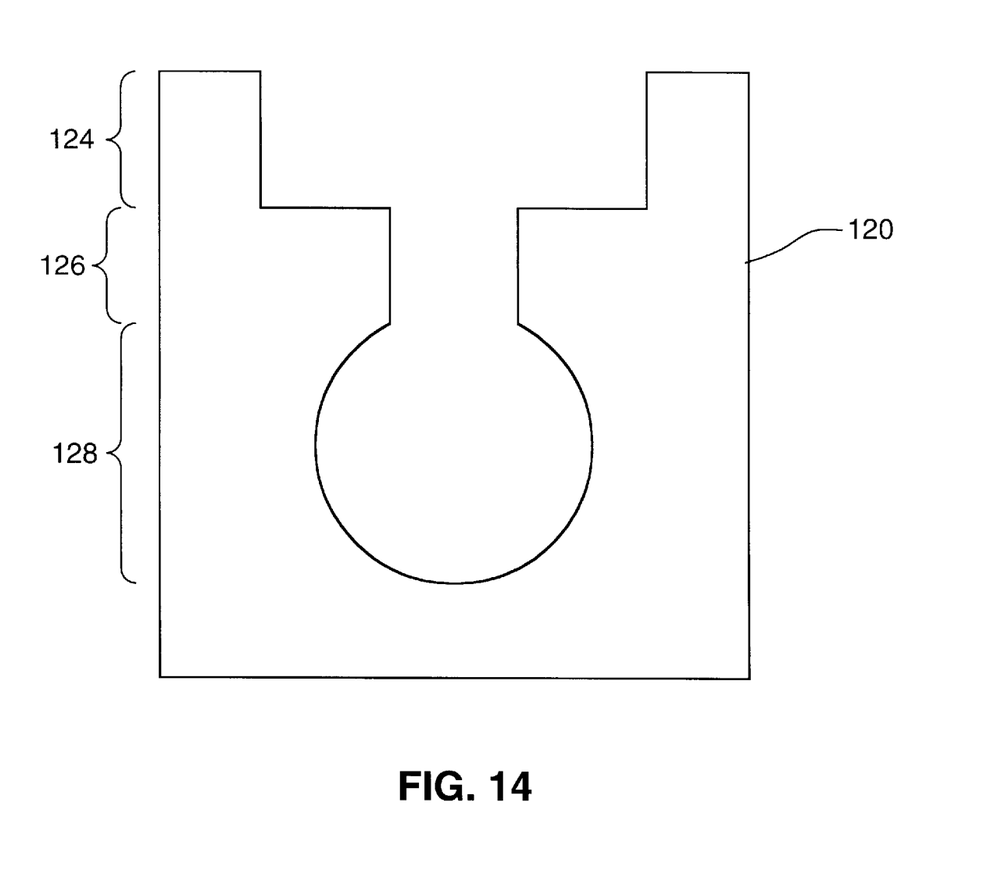
FIG. 14 is a cross-sectional view of a mold suitable for forming the pad of the present invention.

Next, the mesh and pull string structure is removed from the first mold and placed in a longitudinal second mold 120, a cross-section of which is shown in FIG. 14. The second mold 120 has a body space 124, a neck space 126, and a draw cord space 128. The draw cord 86 fits within the draw cord space 128. The other spaces mold a thermoplastic elastomeric material, when it is injected into the second mold, to form the neck 96 and pad body 98 of the pad 80 shown in FIG. 4.

The mesh 110 is again placed into a V-shape in the mold 120. Then, the thermoplastic elastomer is injected into the second mold to form the pad 80 on the draw cord 86 and around the mesh 110. The elastomer is preferably of 30 durometer and shore "A", with a range from approximately 15 to 70 durometer. A preferred elastomer is the brand Kraton from Shell Corp. Other elastomeric materials include silicone and urethane. Alternatively, the neck 96 may be formed from a material different from that of pad body 98, such as plastic.

The triangular clamping surface 100 may be formed by a suitable covering portion of the mold 120. Once the elastomer has cured, the pad 80 is removed from the second mold 120.

In a modified preferred method, the pad 80 may be fabricated with only one web of the mesh 110. Preferably once the draw cord 86 has been attached, one web of the resulting V-shaped mesh 110 is cut off before the pad 80 is molded. This results in a single web mesh structure being formed in the pad 80, instead of the two webs of the V-shaped mesh. Another option is for the draw cord 86 to be attached along one edge of an unfolded web of the mesh 110.

Figure 11:
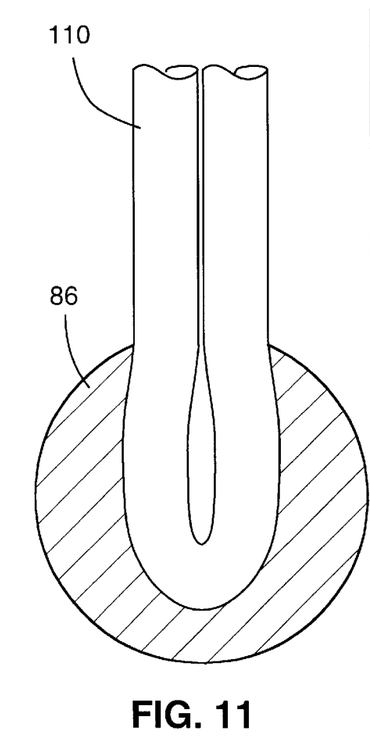
FIG. 11 is a cross-sectional view taken on the plane designated by line 11—11 of FIG. 10.

In a second method, the draw cord 86 is provided and a longitudinal slit is made in the draw cord. The mesh 110 is then folded and the folded edge portion is placed in the slit. FIG. 11 shows a cross-sectional view of this construction. The mesh 110 may then be attached to the draw cord 86 with glue. Then the elastomer is molded as described above in the preferred method.

Figure 12:
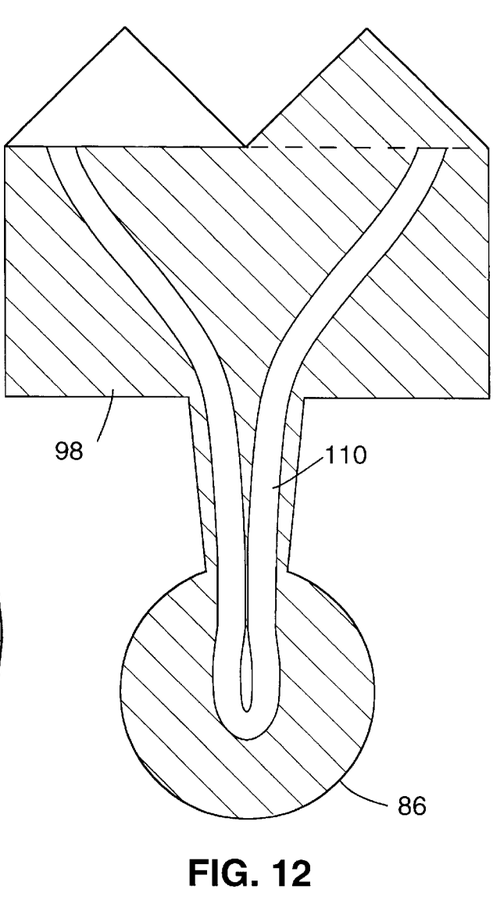
FIG. 12 is a cross-sectional view taken on a plane perpendicular to a longitudinal line of a pad constructed according to a second embodiment of the present invention.

FIG. 12 is a cross-section of the pad 80 showing a preferred orientation of the mesh 110 within the pad. The pad body 98 provides support for the mesh 110. In turn, the mesh 110 provides support for the pad body 98 and neck 96. Thus, the mesh 110 and pad body 98 provide mutual reinforcement. This mutual reinforcement is helpful during the installation process of the pad 80 in the jaw 66. In addition, the mutual reinforcement is helpful when the neck 96 pulls the pad body 98 against the outer surfaces 92 of the jaw 66.

Figure 13:
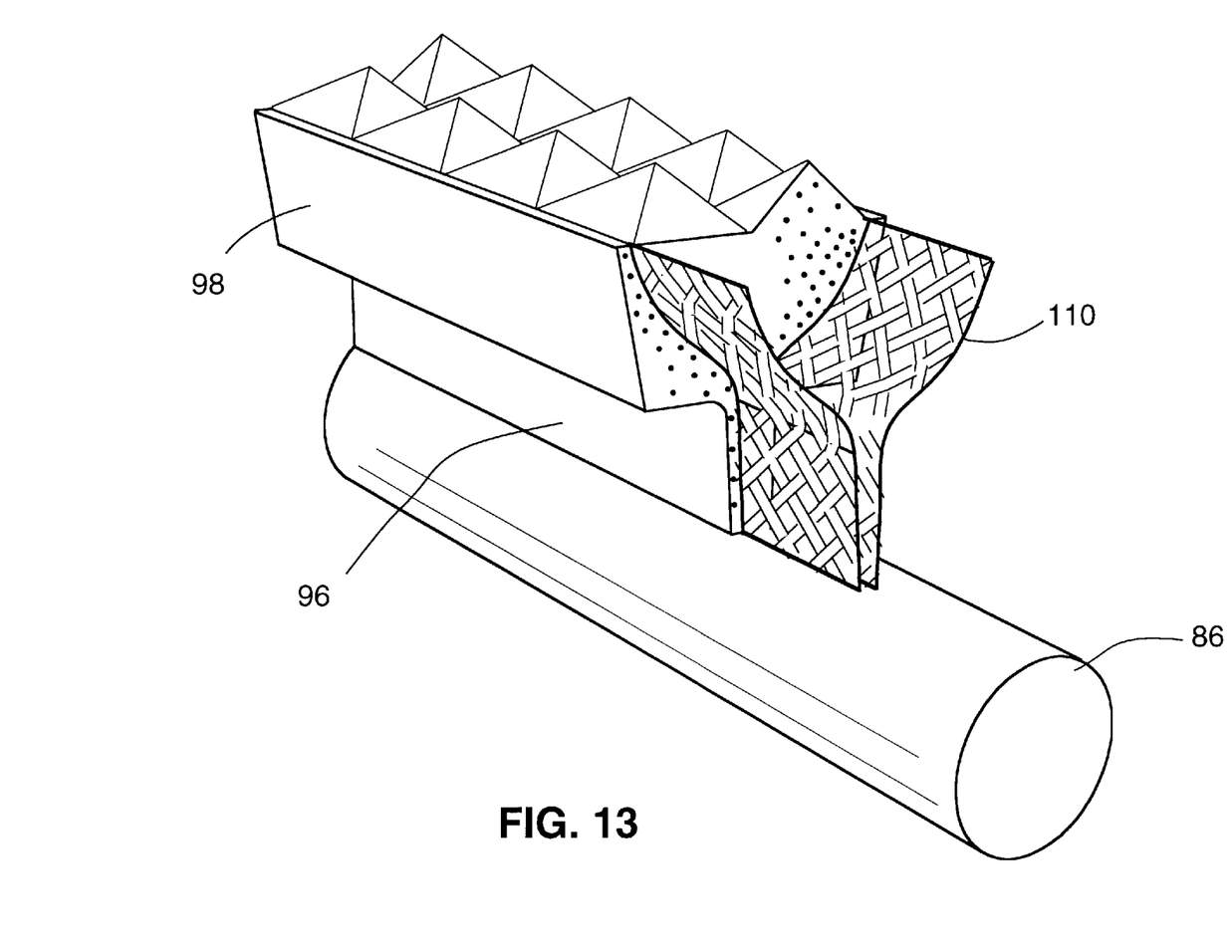
FIG. 13 is a perspective view of the pad of FIG. 12 with portions thereof cut away.

FIG. 13 is a perspective view of pad 80 with portions cut away to show detail. This figure shows that the elastomeric material of the pad body 98 and neck 96 has flowed between the filaments of the mesh 110 during the molding process. Upon curing, the elastomeric material encapsulates the filaments, binding them to one another and to the cured pad, forming a web-like structure. This encapsulation is more fully detailed in the co-pending application Ser. No. 09/336,131 entitled "Surgical Clamp Pads With Elastomer Impregnated Mesh" filed Jun. 18, 1999, commonly owned by the assignee of the present application and incorporated by reference herein. This co-pending application further details that the mesh itself may protrude from the pad body 98 to form the clamping surface 100.

Figure 10A:
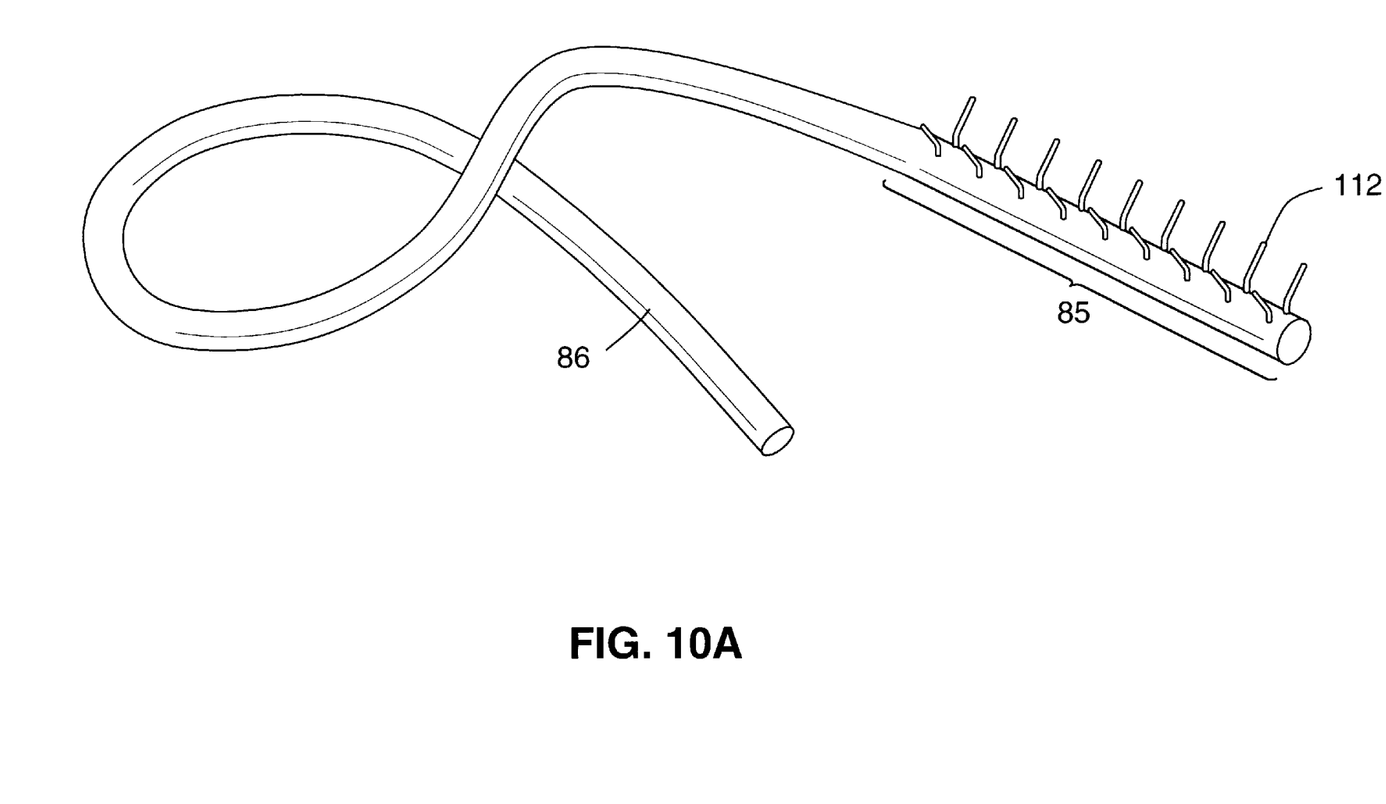
FIG. 10A is a perspective view of a draw cord with stabilizing elements for a third embodiment of the present invention.

FIG. 10A shows that stabilizing elements 112 may be used in place of mesh 110 to internally reinforce the pad. The stabilizing elements 112 may be made from the same thermoplastic elastomer as draw cord 86. The stabilizing elements 112 may be molded concurrently with the molding of draw cord 86. As earlier detailed, the attachment member 85 is preferably the portion of draw cord 86 commensurate with the stabilizing elements 112.

CONCLUSION

From the foregoing detailed description, it is believed that the present invention enables the attainment of the objects initially set forth herein. In particular, the invention provides a surgical clamp having a cavity to receive a replaceable pad. The pad includes a draw cord for easy installation.

Such a surgical clamp has a number of general advantages over many existing clamps in addition to the advantages discussed above. The replaceable pads according to the present invention are sleeker and have a lower profile, and may be made of softer and more delicate materials. Such pads also increase the clamp shapes available to use pads, because many existing pads conform only to straight jaws.

It should be understood that various alternatives to the embodiments of the invention described herein may be employed in practicing the invention. It is intended that the following claims define the scope of the invention and that structures within the scope of these claims and their equivalents are covered thereby.

We claim:

1. A pad configured to attach to a jaw of a surgical clamp, comprising:

an elongate body configured to extend over an outer surface of a jaw of a surgical clamp;

a flexible elongate attachment member connected to said body and configured for slidable receipt within an elongate cavity extending longitudinally of said jaw.

2. The pad of claim 1, wherein said attachment member further comprises:

a plurality of stabilizing elements extending from said attachment member, wherein said stabilizing elements are disposed at least partially within said elongate body to internally reinforce said elongate body.

3. The pad of claim 1, wherein:

said body is flexible and is configured to extend over said outer surface of a curved jaw.

4. The pad of claim 1, further comprising:

a draw cord extending generally longitudinally from one end of said attachment member.

5. The pad of claim 1, further comprising:

a neck connecting said body and said attachment member.

6. The pad of claim 5, wherein:

said neck has a cross-sectional width less than that of said attachment member.

7. The pad of claim 5, further comprising:

a mesh structure within said neck and said body configured to internally reinforce said pad, said mesh structure being secured to said attachment member.

8. The pad of claim 1, further comprising:

a draw cord extending generally longitudinally from one end of said elongate body.

9. A pad configured for attachment to a jaw of a surgical clamp, said clamp having an elongate attaching element extending longitudinally along said jaw, said pad comprising:

a flexible elongate body configured to extend over an outer surface of said jaw; and a flexible elongate attachment member connected to said body, said attachment member being engagable with said attaching element and configured for slidable receipt and securement onto said jaw.

* * * * *